US012287294B2

(12) United States Patent
Ouyang et al.

(10) Patent No.: US 12,287,294 B2
(45) Date of Patent: Apr. 29, 2025

(54) PREPARATION METHOD OF NANOSCALED DYE@ZIF-8-BASED COLORIMETRIC SENSOR AND APPLICATION THEREOF IN FOOD QUALITY EVALUATION

(71) Applicant: JIANGSU UNIVERSITY, Zhenjiang (CN)

(72) Inventors: Qin Ouyang, Zhenjiang (CN); Yu Wang, Zhenjiang (CN); Yanna Rong, Zhenjiang (CN); Quansheng Chen, Zhenjiang (CN); Hao Lin, Zhenjiang (CN); Zhiming Guo, Zhenjiang (CN)

(73) Assignee: JIANGSU UNIVERSITY, Zhenjiang (CN)

( * ) Notice: Subject to any disclaimer, the term of this patent is extended or adjusted under 35 U.S.C. 154(b) by 0 days.

(21) Appl. No.: 18/799,818

(22) Filed: Aug. 9, 2024

(65) Prior Publication Data
US 2024/0402089 A1 Dec. 5, 2024

(51) Int. Cl.
G01N 33/02 (2006.01)
B01L 3/00 (2006.01)
(Continued)

(52) U.S. Cl.
CPC ............ *G01N 21/78* (2013.01); *B01L 3/5023* (2013.01); *B01L 3/502707* (2013.01);
(Continued)

(58) Field of Classification Search
CPC .. G01N 33/02; G01N 33/54373; G01N 21/78; G01N 21/80; G01N 21/79; G01N 21/65; G01N 21/658; G01J 3/46; G01J 3/462; G01J 3/463; G01J 3/02; G01J 3/0264; G01J 2003/468; B82Y 10/00; B82Y 5/00; G01C 11/00; G06F 11/263; G06F 11/273
(Continued)

(56) References Cited

U.S. PATENT DOCUMENTS

2015/0191491 A1* 7/2015 Shieh ...................... C07F 3/003
548/103

FOREIGN PATENT DOCUMENTS

CN 110333229 A 10/2019
CN 109164076 B * 1/2021 ......... G01N 21/6428
(Continued)

OTHER PUBLICATIONS

Feng Zhang et al., "Preparation and application of metal-organic framework films", Scientia Sinica Chimica, vol. 43, No. 12, Dec. 20, 2013, pp. 1748-1760.

*Primary Examiner* — Jeffrey P Aiello

(57) ABSTRACT

A method of preparing a nanoscaled dye@ZIF-8-based colorimetric sensor is provided, in which a ZIF-8 nanomaterial is first prepared from $Zn(CH_3COO)_2$ and the 2-methylimidazole, and then the ZIF-8 nanomaterial is dispersed with ethanol and mixed with a colorimetric solution. The resultant mixed solution is added with polyethylene glycol-300 and applied to a substrate to obtain the nanoscaled dye@ZIF-8-based colorimetric sensor. This application further provides an evaluation method using the nanoscaled dye@ZIF-8-based colorimetric sensor, in which a back propagation neural network is established as the food quality evaluation model to evaluate the food quality.

8 Claims, 13 Drawing Sheets

(51) Int. Cl.
*G01J 3/46* (2006.01)
*G01N 21/78* (2006.01)

(52) U.S. Cl.
CPC .......... *G01N 33/02* (2013.01); *B01L 2200/16* (2013.01); *B01L 2300/0654* (2013.01); *B01L 2300/069* (2013.01)

(58) Field of Classification Search
USPC ........ 73/861.04; 356/301, 300, 315; 702/23, 702/22, 27, 29, 30, 32, 57, 85, 108, 127, 702/50, 120; 977/700, 839, 902, 734, 977/742, 773
See application file for complete search history.

(56) References Cited

FOREIGN PATENT DOCUMENTS

| | | | | |
|---|---|---|---|---|
| CN | 113151243 A | | 7/2021 | |
| CN | 113731486 A | | 12/2021 | |
| CN | 114441458 A | * | 5/2022 | ............. G01N 21/31 |
| CN | 115216509 A | | 10/2022 | |

* cited by examiner

PREPARATION METHOD OF NANOSCALED DYE@ZIF-8-BASED COLORIMETRIC SENSOR AND APPLICATION THEREOF IN FOOD QUALITY EVALUATION

CROSS-REFERENCE TO RELATED APPLICATIONS

This application claims the benefit of priority from Chinese Patent Application No. 202311018595.9, filed on Aug. 14, 2023. The content of the aforementioned application, including any intervening amendments thereto, is incorporated herein by reference in its entirety.

TECHNICAL FIELD

This application relates to food non-destructive detection, and more particularly to a preparation method of a nanoscaled dye@ZIF-8-based colorimetric sensor and an application thereof in food quality evaluation.

BACKGROUND

Food quality, involving multiple evaluation indicators such as appearance, texture, aroma, flavor and nutrient content, is used to evaluate the quality of food products. The food quality is closely related to the acceptability of the food, and significantly affects the benefits obtained from production to consumption. Therefore, the scientific and systematic evaluation of food quality is particularly important.

Flavor is considered as an important indicator to evaluate the food quality. The food flavor can be evaluated subjectively or objectively. The subjective evaluation is represented by sensory evaluation, in which the food quality is evaluated through the stimulation of the food flavor on human sensory organs. At present, the sensory evaluation method is still the most direct method to evaluate the food quality. However, the sensory evaluation presents strong subjectivity and poor reproducibility since it is easily affected by the physiological state and the learning degree of the sensory evaluator and the environment. The objective evaluation is based on instrumental measurement, and external and internal qualities of food products are analyzed according to measurement results. Among the modern instrumental analysis techniques, gas chromatography-mass spectrometry (GC-MS) is employed to accurately and objectively detect and analyze volatile components of food products. However, this method struggles with time-consuming and cumbersome operation.

Therefore, it is of great significance to provide a method that can realize the rapid detection and analysis of food quality.

SUMMARY

In view of the deficiencies in the prior art, such as complicated detection process, high subjectivity and low sensitivity, this application provides a rapid food quality evaluation method based on a nanoscaled dye@ZIF-8-based colorimetric sensor.

Technical solutions of this application are described as follows.

In first aspect, this application provides a method of preparing a nanoscaled dye@ZIF-8-based colorimetric sensor, comprising:

Step I Preparation of ZIF-8 Nanomaterials (a) dissolving $Zn(CH_3COO)_2·2H_2O$ in deionized water to obtain a $Zn(CH_3COO)_2$ solution, wherein a ratio of a weight of the $Zn(CH_3COO)_2·2H_2O$ to a volume of the deionized water is 2.70 g: 45 mL; and dissolving 2-methylimidazole in deionized water to obtain a 2-methylimidazole solution, wherein a ratio of a weight of the 2-methylimidazole to a volume of the deionized water is 22.23 g: 100 mL;

(b) mixing the $Zn(CH_3COO)_2$ solution and the 2-methylimidazole solution following by stirring and standing to obtain a precipitate, wherein a volume ratio of the $Zn(CH_3COO)_2$ solution to the 2-methylimidazole solution is 45:57.6, the stirring is performed for 10-20 min, and the standing is performed for 2-6 h; and subjecting the precipitate to centrifugal washing for 3-5 times with water and ethanol, respectively, and drying to obtain a zeolitic imidazolate framework-8 (ZIF-8) nanomaterial;

Step II Preparation of Nanoscaled Dye@ZIF-8 Colorimetric Materials and the Nanoscaled Dye@ZIF-8-Based Colorimetric Sensor (a1) dispersing the ZIF-8 nanomaterial with ethanol to obtain a ZIF-8 dispersion with a concentration of 2 mg/mL;

(b1) preparing a colorimetric solution with a concentration of 2 mg/mL, wherein the colorimetric solution is a pH indicator ethanol solution or a metalloporphyrin dichloromethane solution;

(c1) mixing the colorimetric solution with the ZIF-8 dispersion in a certain proportion to obtain a mixed solution;

(d1) adding polyethylene glycol-300 to the mixed solution followed by ultrasonic treatment to obtain the nanoscaled dye@ZIF-8 colorimetric material; and (f1) fixing the nanoscaled dye@ZIF-8 colorimetric material on a substrate to obtain a nanoscaled dye@ZIF-8-based colorimetric sensor; and sealing the nanoscaled dye@ZIF-8-based colorimetric sensor in a sealed bag for backup.

In an embodiment, X kinds of colorimetric solutions are prepared, and X is a positive integer. The X colorimetric solutions comprise a pH indicator ethanol solution, a metalloporphyrin dichloromethane solution, and a combination thereof. A ratio of a weight of a pH indicator to a volume of ethanol in the pH indicator ethanol solution is 20 mg: 10 mL; and a ratio of a weight of a metalloporphyrin compound to a volume of dichloromethane in the metalloporphyrin dichloromethane solution is 20 mg: 10 mL.

In an embodiment, the colorimetric solution and the ZIF-8 dispersion are mixed in a volume ratio of 1:1. The polyethylene glycol-300 is 20% by volume of the mixed solution.

In an embodiment, the pH indicator is selected from the group consisting of cresol red, brilliant yellow, and neutral red; and the metalloporphyrin compound is selected from the group consisting of 2, 3, 7, 8, 12, 13, 17, 18-octaethyl-21H, 23H-porphine nickel (II), 5, 10, 15, 20-tetraphenyl-21H,23H-porphine zinc, and 5, 10, 15, 20-tetrakis(pentafluorophenyl)-21H, 23H-porphyrin iron (III) chloride.

In an embodiment, in step (d1), the ultrasonic treatment is performed at 40° C. for 30-50 min; a volume of the nanoscaled dye@ZIF-8 colorimetric material applied to the substrate is 1.5-2 μL; and the substrate is a silica gel plate, a Polyvinylidene Fluoride (PVDF) membrane, or a mixed cellulose ester.

In second aspect, this application provides a food quality evaluation method using the above nanoscaled dye@ZIF-8-based colorimetric sensor, comprising:

(1) Establishment of Food Quality Evaluation Model
  (A) selecting a plurality of reference samples respectively at a plurality of quality grades, wherein the plurality of quality grades respectively correspond to different volatile odorants; the nanoscaled dye@ZIF-8-based colorimetric sensor is configured to present different colors respectively in the presence of the different volatile odorants; each of the plurality of reference samples is an agricultural product or an aquatic product; and an indicator for characterizing the plurality of quality grades is freshness or sensory quality;
  (B) capturing, by a camera, the nanoscaled dye@ZIF-8-based colorimetric sensor to obtain a first image;
  respectively placing the plurality of reference samples in a reaction vessel with the nanoscaled dye@ZIF-8-based colorimetric sensor to allow the nanoscaled dye@ZIF-8-based colorimetric sensor to react with volatile odorants respectively released from the plurality of reference samples, wherein the reaction vessel is kept sealed during a reaction;
  capturing, by the camera, a reacted nanoscaled dye@ZIF-8-based colorimetric sensor to obtain a second image, and saving the second image in a computer;
  locating, by the computer, each of color-sensitive units of the nanoscaled dye@ZIF-8-based colorimetric sensor respectively from the first image and the second image; extracting a color feature of each of the color-sensitive units; and obtaining the difference in grayscale value for each channel before and after the reaction from each color-sensitive unit as feature variables of each of the color-sensitive units; and
  combining feature variables of the plurality of reference samples to obtain a feature matrix; and constructing a back propagation neural network (BPNN) model with the feature matrix as an input and the plurality of quality grades as an output as a food quality evaluation model; and (2) Rapid Evaluation of Food Quality
  reacting a to-be-tested sample with the nanoscaled dye@ZIF-8-based colorimetric sensor according to the step (B) to obtain a feature variable of the to-be-tested sample; and inputting the feature variable of the to-be-tested sample into the BPNN model to obtain quality grade information of the to-be-tested sample, and evaluating quality of the to-be-tested sample based on the quality grade information.

In an embodiment, in the step (B), when the plurality of reference samples are agricultural products, an amount of each of the plurality of reference samples added to the reaction vessel is 2-5 g; when the plurality of reference samples are aquatic products, an amount of each of the plurality of reference samples added to the reaction vessel is 10-15 g; the nanoscaled dye@ZIF-8-based colorimetric sensor is reacted with the volatile odorants for 10-20 min; and the nanoscaled dye@ZIF-8-based colorimetric sensor is provided at a top of the reaction vessel.

In an embodiment, in the step (B), the feature variables of each of the color-sensitive units is extracted through steps of:
  locating, by the computer, each of the color-sensitive units;
  decomposing each of the first image and the second image into three grayscale images respectively representing a red (R)-channel grayscale sub-image, a green (G)-channel grayscale sub-image, and a blue (B)-channel grayscale sub-image;
  obtaining the difference in grayscale value for each channel before and after the reaction from each of the color-sensitive units, expressed as: $\Delta R = R_a - R_b$, $\Delta G = G_a - G_b$, and $\Delta B = B_a - B_b$, wherein a subscript a represents a grayscale value from the second image, and a subscript b represents a grayscale value from the first image; and
  calculating a Euclidean distance, expressed as:

$$ED = \sqrt{\Delta R^2 + \Delta G^2 + \Delta B^2}\,;$$

wherein $\Delta R$, $\Delta G$, $\Delta B$, and ED are the feature variables of each of the color-sensitive units; when the number of the color-sensitive units is X, there are a total of Y feature variables, wherein Y=4X.

In an embodiment, in the step (B), the number of the plurality of reference samples for constructing the food quality evaluation model is N; the number of the plurality of quality grades is n; and the number of reference samples in each of the plurality of quality grades is m, N=n×m; n is a positive integer not less than 2; and both m and N are positive integers.

In an embodiment, in the step (B), the food quality evaluation model is built through steps of:
  constructing the feature matrix S, wherein S=N×Y, N represents the number of the plurality of reference samples, and Y represents the number of feature variables in X color-sensitive units; and
  constructing the BPNN model with the feature matrix S as the input and a quality grade matrix T corresponding to the plurality of reference samples as the output;
  wherein the feature matrix S is expressed as:

$$S = \begin{bmatrix} S_{11} & S_{12} & \ldots & S_{1Y} \\ S_{21} & S_{22} & \ldots & S_{2Y} \\ \vdots & \vdots & \vdots & \vdots \\ S_{N1} & S_{N2} & \ldots & S_{NY} \end{bmatrix};$$

and
  the quality grade matrix T is expressed as:

$$T = \begin{bmatrix} T_{11} \\ T_{21} \\ \vdots \\ T_{N1} \end{bmatrix}.$$

In an embodiment, the step of "evaluating quality of the to-be-tested sample" is performed through steps of:
  obtaining the feature variable of the to-be-tested sample according to the step (B), wherein the number of the to-be-tested sample is M, and the number of the feature variable of each of M to-be-tested samples is Y; and constructing a feature variable matrix R, wherein R=M×Y; and
  inputting the feature variable matrix R into the BPNN model constructed in the step (B) to generate an output matrix $Q$ corresponding to quality grade information of the M to-be-tested samples for food quality evaluation;

wherein the feature variable matrix R is expressed as:

$$R = \begin{bmatrix} R_{11} & R_{12} & \ldots & R_{1Y} \\ R_{21} & R_{22} & \ldots & R_{2Y} \\ \vdots & \vdots & \vdots & \vdots \\ R_{M1} & R_{M2} & \ldots & R_{MY} \end{bmatrix};$$

and the output matrix $Q$ is expressed as:

$$Q = \begin{bmatrix} Q_{11} \\ Q_{21} \\ \vdots \\ Q_{M1} \end{bmatrix}.$$

The beneficial effects of the present application are described as follows.

(1) This application enables the controllable preparation of a nanoscaled dye@ZIF-8-based colorimetric sensor, and by means of the dye@ZIF-8-based colorimetric sensor, the volatile composition information of a food sample can be obtained, thereby facilitating the rapid quality evaluation of the food sample.

(2) The color-sensitive materials undergo coordination with the volatile components released from the food sample to generate complexes, which further alter the molecular structure of the color-sensitive materials and cause a change in the color presented by the color-sensitive materials.

(3) The application prepares a nanoscaled dye@ZIF-8-based colorimetric sensor by coupling ZIF-8 with the color-sensitive material (pH indicator and metalloporphyrin), where the ZIF-8 surface contains unsaturated ligand-binding sites, which can form a complex with the volatile compounds to adsorb the volatile compounds, thereby improving the detection sensitivity.

(4) In this application, the back propagation neural network (BPNN) model is established for rapid evaluation of food quality, where signal values collected by the nanoscaled dye@ZIF-8-based colorimetric sensor are taken as the input, and food grade information is taken as the output. The BPNN model has good generality, and can improve the evaluation efficiency of food quality, and thus it is of great significance for the evaluation of food quality.

DETAILED DESCRIPTION OF EMBODIMENTS

The present disclosure will be further described in detail below in conjunction with the accompanying drawings and embodiments, which are not intended to limit the disclosure, but should be understood as a more detailed description of certain aspects, features, and solutions of the present disclosure.

As used herein, the terms are intended only to describe some embodiments and are not intended to limit the disclosure. Unless otherwise defined, all technical and scientific terms used herein have the same meaning as those commonly understood by those skilled in the art.

Described herein are only preferred methods and materials, and any methods and materials similar or equivalent to those described herein may also be used for the implementation or test of the present disclosure. All literatures in the description are incorporated by reference for describing the methods and/or materials associated with the literatures. In the event of any divergence with any incorporated literature, the contents of this disclosure shall prevail.

Various modifications, replacements, and variations of embodiments in this disclosure made by those skilled in the art without departing from the spirit of the disclosure should fall within the scope of the disclosure defined by the appended claims.

For those skilled in the art, other embodiments obtained based on these embodiments without paying creative efforts should fall within the scope of the disclosure defined by the appended claims.

Embodiment 1

A method of preparing a nanoscaled dye@ZIF-8-based colorimetric sensor included the following steps.

Step I Preparation of ZIF-8 Nanomaterials $Zn(CH_3COO)_2 \cdot 2H_2O$ and 2-methylimidazole powder were dissolved in deionized water, respectively, thereby obtaining $Zn(CH_3COO)_2$ solution and 2-methylimidazole solution, respectively. The ratio of a weight of $Zn(CH_3COO)_2 \cdot 2H_2O$ to a volume of deionized water was 2.70 g: 45 mL, and the ratio of a weight of 2-methylimidazole to a volume of deionized water was 22.23 g: 100 mL.

$Zn(CH_3COO)_2$ solution and 2-methylimidazole solution were mixed according to a volume ratio of 45:57.6, then stirred for 20 min after mixing, and then stood for 4 h to obtain the precipitate. The precipitate was washed 3 times with water and ethanol, respectively, centrifuged, and then dried to a constant weight in an oven to obtain a zeolitic imidazolate framework-8 (ZIF-8) nanomaterial.

Figure 1:
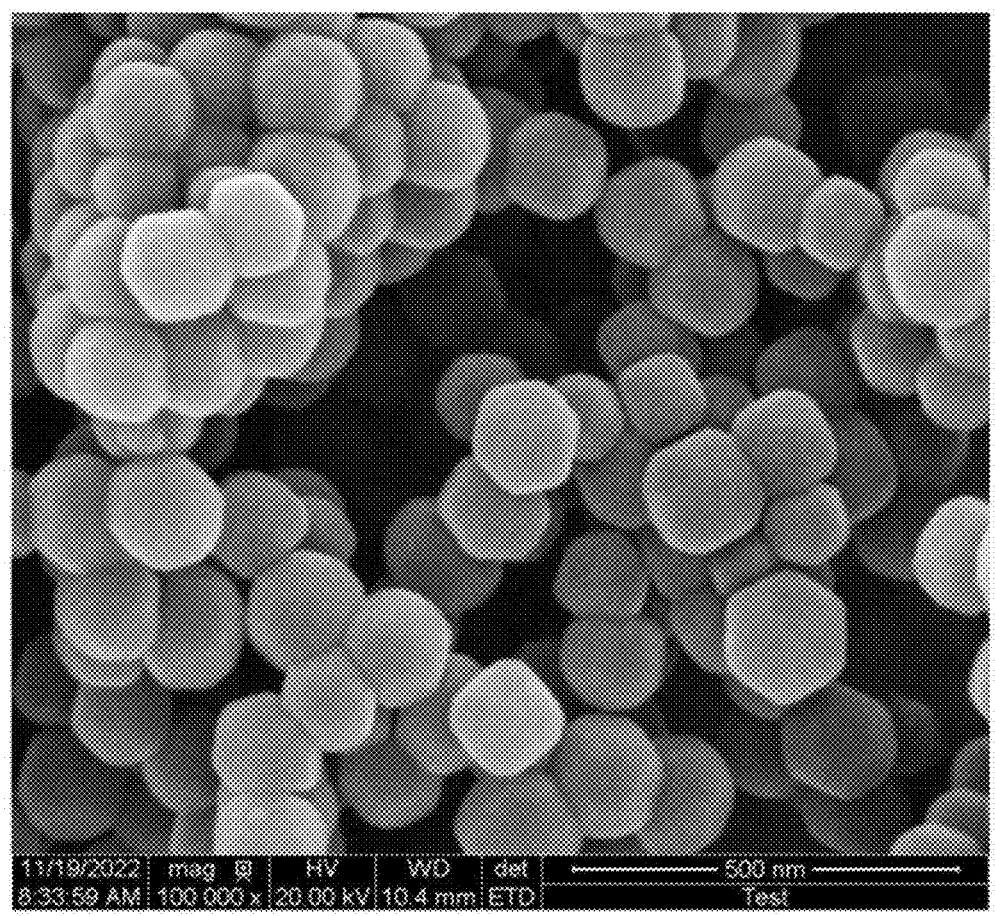
FIG. 1 is a scanning electron microscope (SEM) image of ZIF-8 nanomaterials according to one embodiment of the present disclosure.

FIG. 1 was a scanning electron microscope image (SEM) of ZIF-8 nanomaterials. FIG. 1 showed that the prepared ZIF-8 nanomaterials present regular dodecahedrons with smooth surface and uniform size. This regular dodecahedron structure can provide more adsorption sites for adsorbing volatile substances and improve the enrichment rate of volatile substances.

Figure 2:
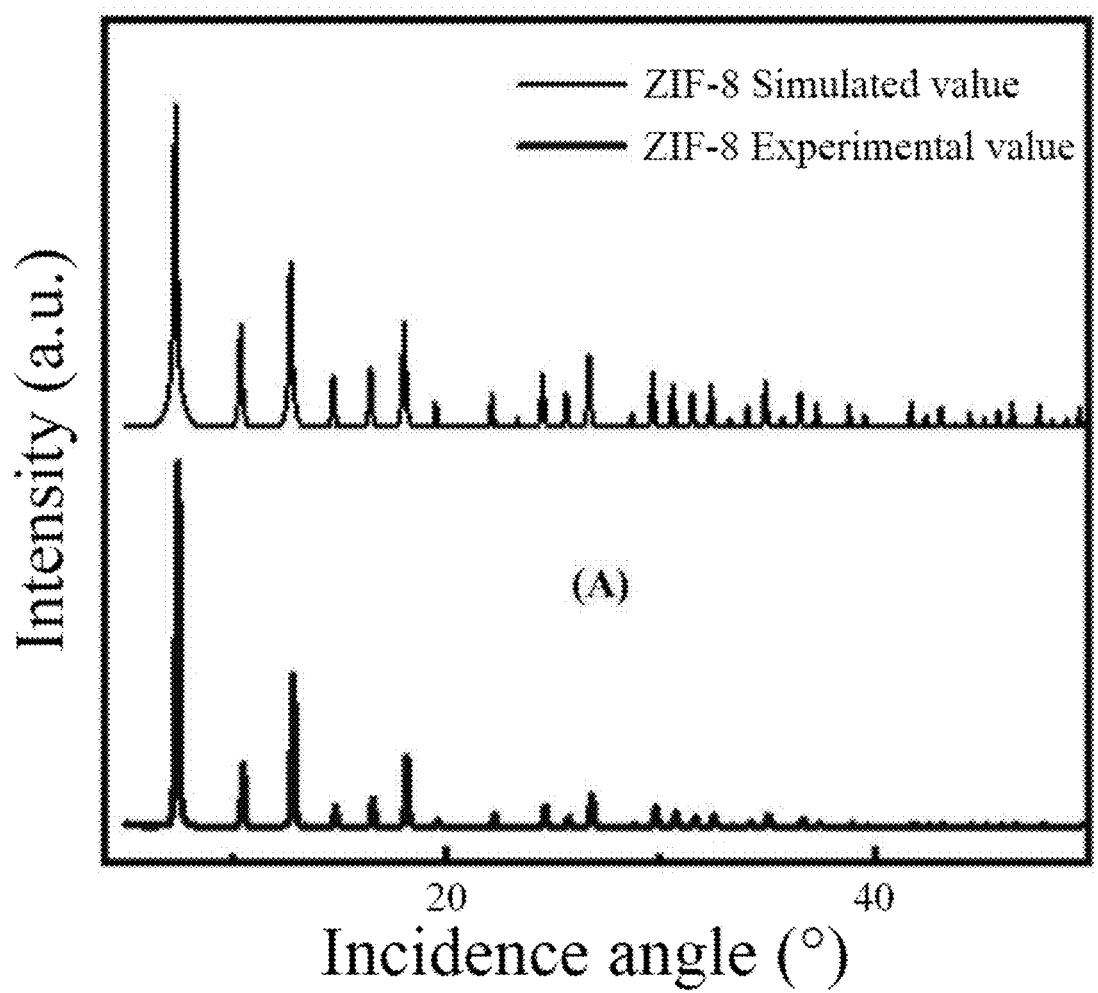
FIG. 2 is an X-Ray Diffraction (XRD) pattern of the ZIF-8 nanomaterials according to one embodiment of the present disclosure.

FIG. 2 was an X-ray Diffraction (XRD) pattern of ZIF-8 nanomaterials. FIG. 2 showed that characteristic peaks of the prepared ZIF-8 nanomaterials were highly consistent with those of the simulated cards, which indicated that the prepared ZIF-8 nanomaterials had high purity and degree of crystallinity.

Figure 3:
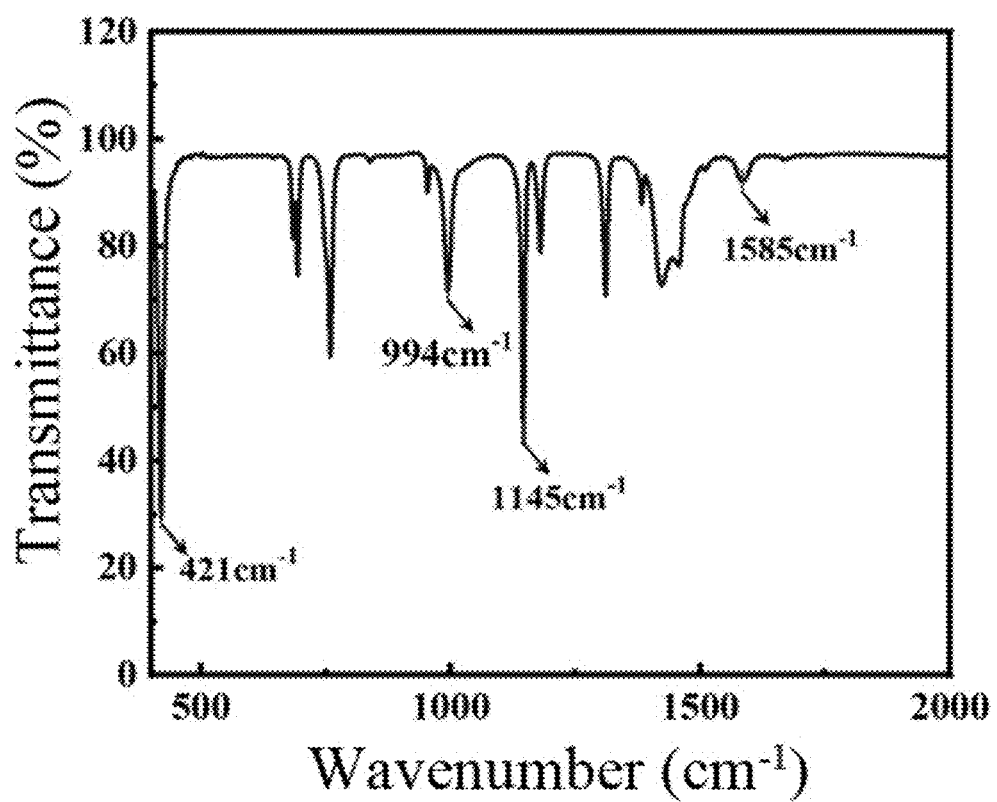
FIG. 3 is a Fourier transform infrared (FTIR) spectrum of the ZIF-8 nanomaterials according to one embodiment of the present disclosure.
Figure 4A:
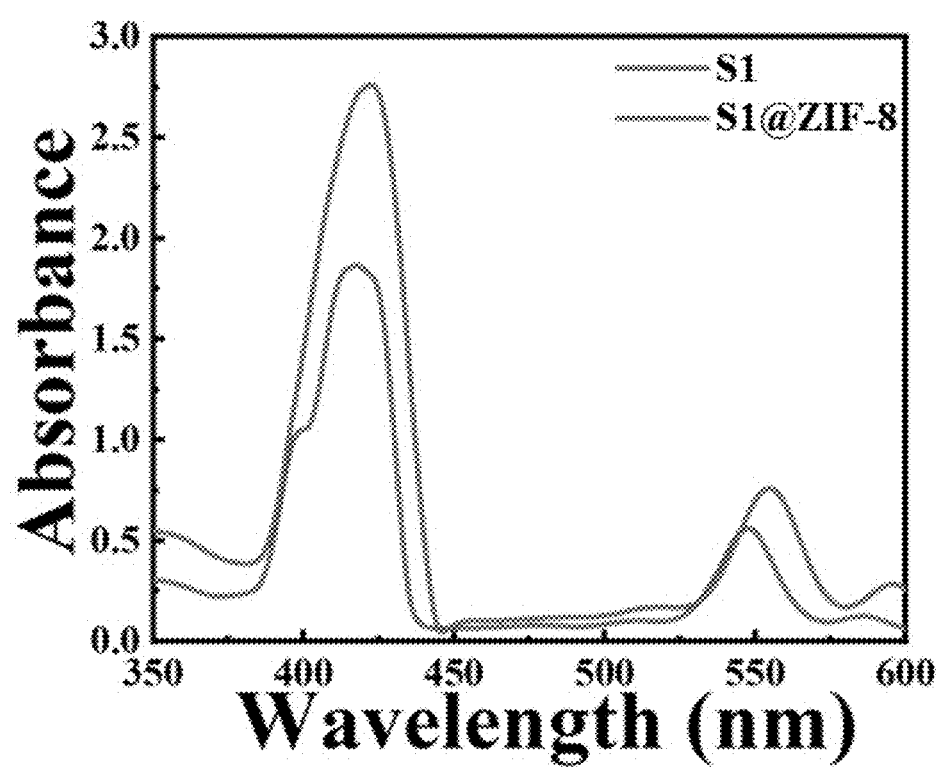
FIGS. 4a-4f are ultraviolet (UV)-visible spectra of nanoscaled dye@ZIF-8-based colorimetric materials according to one embodiment of the present disclosure, where 4a: S1 and S1@ZIF-8; 4b: S2 and S2@ZIF-8; 4c: S3 and S3@ZIF-8; 4d: S4 and S4@ZIF-8; 4e: S5 and S5@ZIF-8; 4f: S6 and S6@ZIF-8.
Figure 4B:
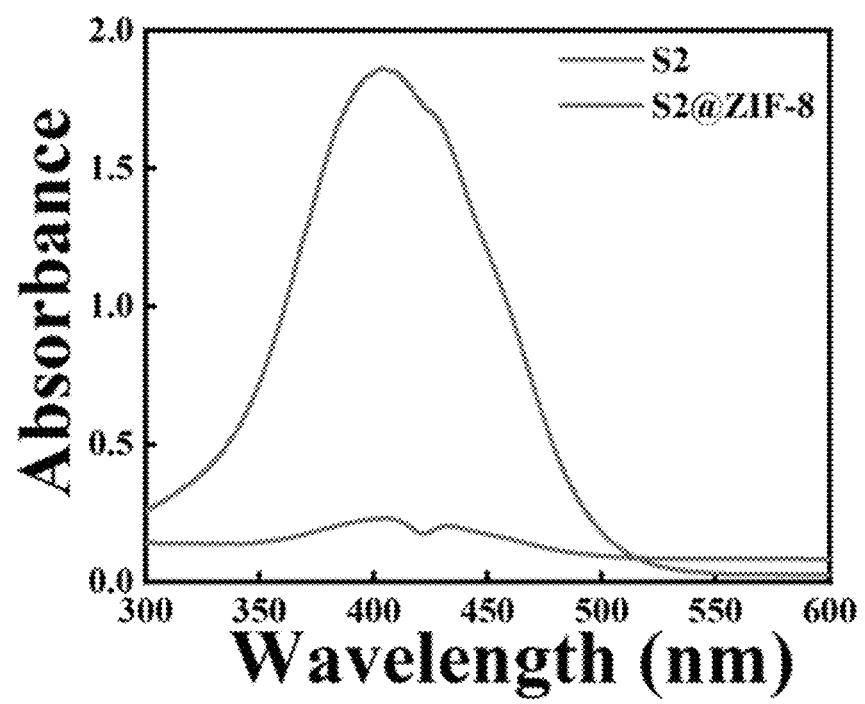
Figure 4C:
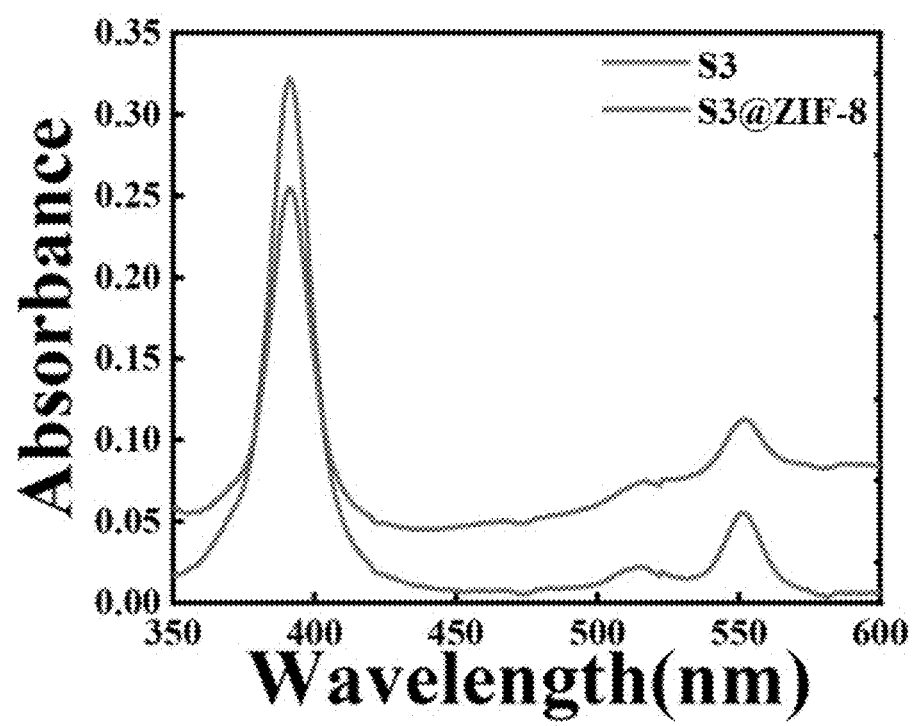
Figure 4D:
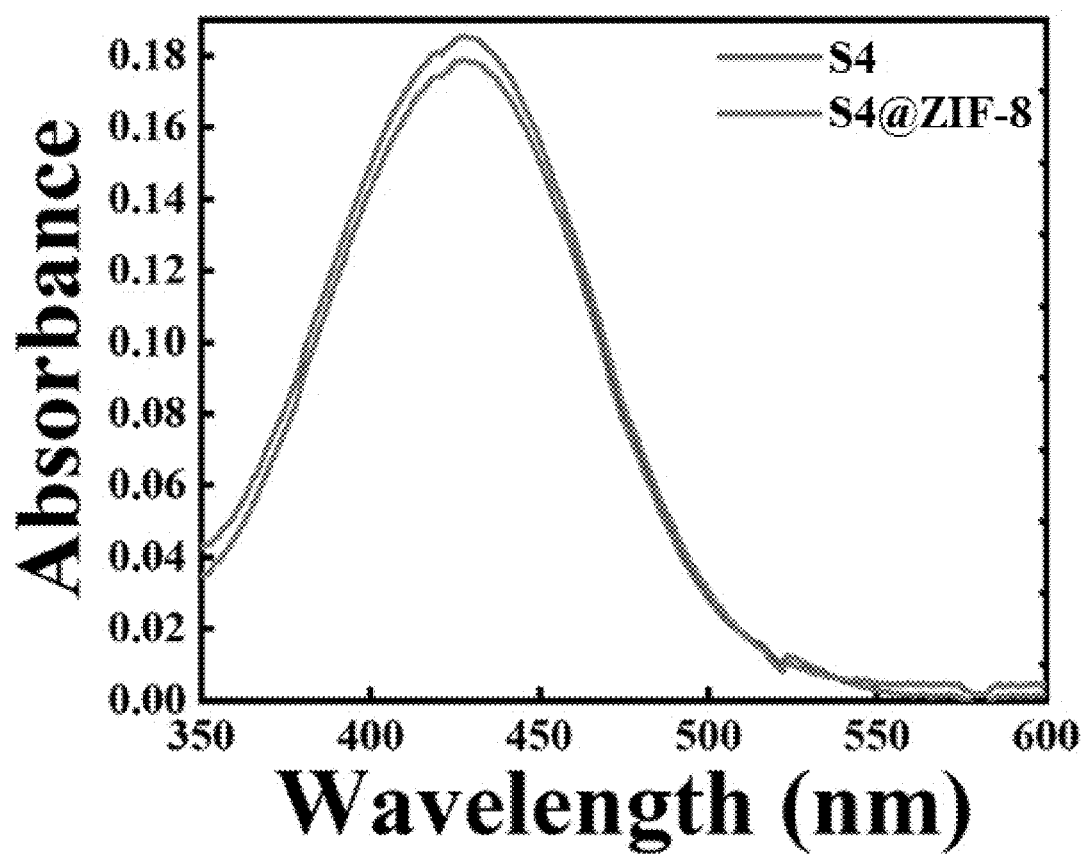
Figure 4E:
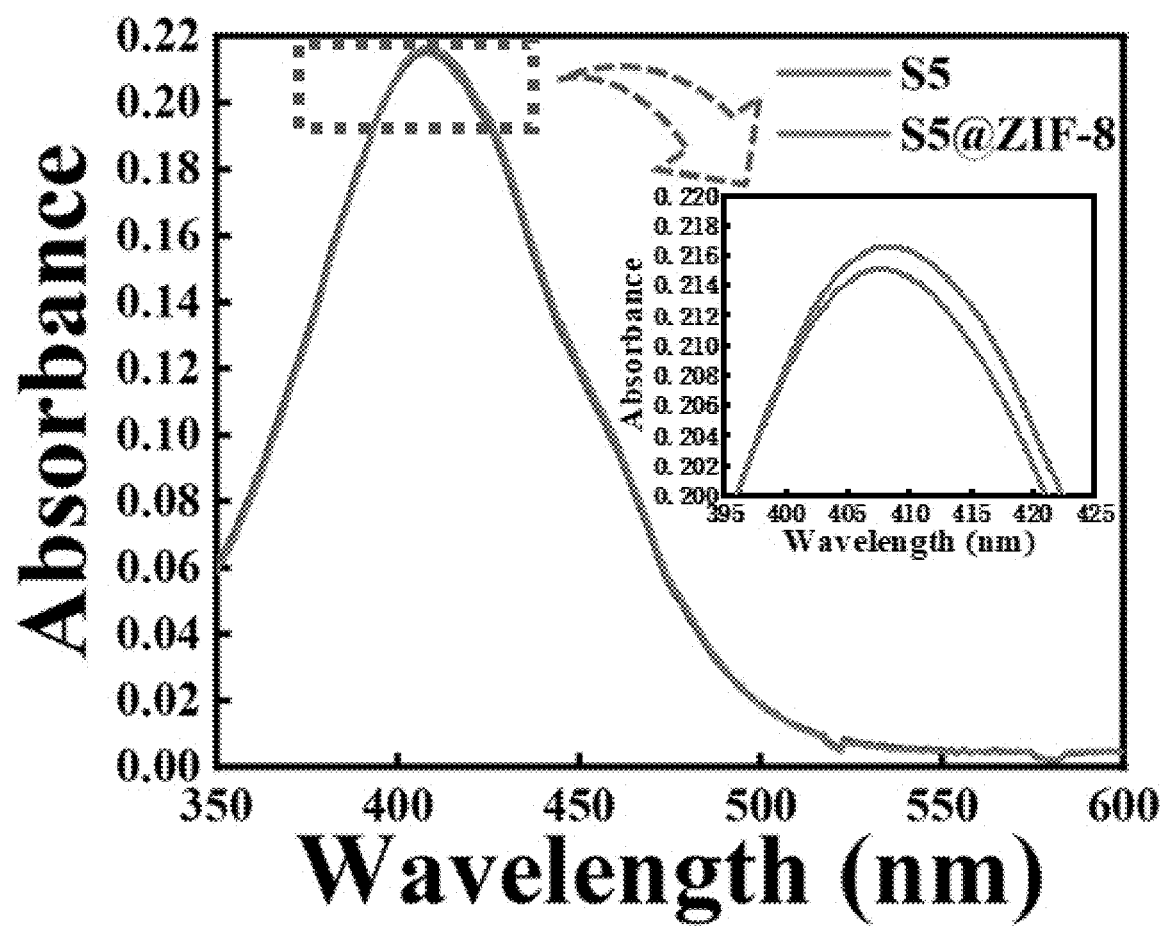
Figure 4F:
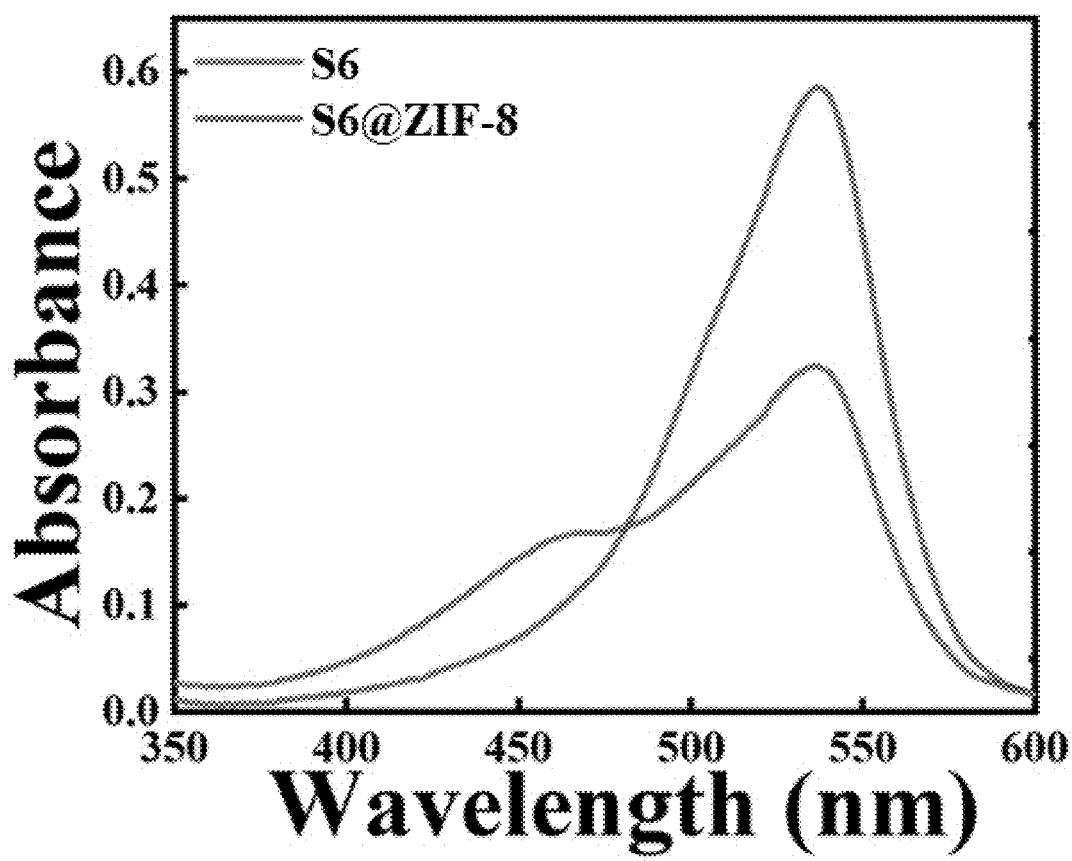

FIG. 3 showed a Fourier transform infrared (FTIR) spectrum of ZIF-8 nanomaterials. FIG. 3 showed that the characteristic absorption peaks due to Zn—N stretching vibration appeared at 421 $cm^{-1}$, and the characteristic peaks due to C=N and C—N vibrations appeared at 994, 1145 and 1585 $cm^{-1}$. All the above tests confirmed the successful synthesis of ZIF-8 nanomaterials.

Step II Preparation of Nanoscaled Dye@ZIF-8 Colorimetric Materials and a Colorimetric Sensor The ZIF-8 nanomaterials prepared in step 1 were dispersed with ethanol to obtain a ZIF-8 dispersion, and the ratio of a weight of ZIF-8 nanomaterials and a volume of ethanol was 20 mg: 10 mL.

Six colorimetric solutions were prepared, including three pH indicator ethanol solutions and three metalloporphyrin dichloromethane solutions.

The six colorimetric solutions were denoted as colorimetric solution 1 (S1), colorimetric solution 2 (S2), colorimetric solution 3 (S3), colorimetric solution 4 (S4), colorimetric solution 5 (S5), and colorimetric solution 6 (S6).

The colorimetric solution 1 was an ethanol solution of cresol red, and the ratio of the weight of cresol red to the volume of ethanol was 20 mg: 10 mL.

The colorimetric solution 2 was an ethanol solution of brilliant yellow, and the ratio of the weight of brilliant yellow to the volume of ethanol was 20 mg: 10 mL.

The colorimetric solution 3 was an ethanol solution of neutral red, and the ratio of the weight of neutral red to the volume of ethanol was 20 mg: 10 mL.

The colorimetric solution 4 was a dichloromethane solution of 2,3,7,8,12,13,17,18-octaethyl-21H, 23H-porphine nickel (II), and the ratio of the weight of 2,3,7,8,12,13,17,18-octaethyl-21H, 23H-porphine nickel (II) to the volume of ethanol was 20 mg: 10 mL.

The colorimetric solution 5 was a dichloromethane solution of 5, 10, 15, 20-tetraphenyl-21H,23H-porphine zinc, and the ratio of the weight of 5, 10, 15, 20-tetraphenyl-21H, 23H-porphine zinc to the volume of ethanol was 20 mg:10 mL.

The colorimetric solution 6 was a dichloromethane solution of 5, 10, 15, 20-tetrakis(pentafluorophenyl)-21H, 23H-porphyrin iron (III) chloride, and the ratio of the weight of 5, 10, 15, 20-tetrakis(pentafluorophenyl)-21H, 23H-porphyrin iron (III) chloride to the volume of ethanol was 20 mg: 10 mL.

Such 6 colorimetric solutions were respectively mixed with ZIF-8 dispersion according to a volume ratio of 1:1 to obtain 6 kinds of mixed solutions. Individual mixed solutions were added with polyethylene glycol-300 (the polyethylene glycol-300 is 20% by volume of each mixed solution), and subjected to ultrasonic treatment at 40° C. for 30 min to allow complete reaction to arrive at six kinds of nanoscaled dye@ZIF-8 colorimetric materials, S1@ZIF-8, S2@ZIF-8, S3@ZIF-8, S4@ZIF-8, S5@ZIF-8, and S6@ZIF-8.

2 μL of individual nanoscaled dye@ZIF-8 colorimetric materials were transferred by a microcapillary tube to be fixed on a silica gel plate to prepare the corresponding nanoscaled dye@ZIF-8-based colorimetric sensor.

Ultraviolet (UV)-visible spectra of the 6 kinds of nanoscaled dye@ZIF-8-based colorimetric materials and their corresponding original colorimetric materials were respectively shown in FIGS. 4a-4f Compared with the original colorimetric materials, absorption peaks of nanoscaled dye@ZIF-8 colorimetric materials in the UV-vis spectra were red-shifted, cleaved or broadened. Moreover, the shape of the absorption peaks remained almost unchanged, confirming the successful synthesis of the nanoscaled dye@ZIF-8 colorimetric materials.

Embodiment 2

Application of the nanoscaled dye@ZIF-8-based colorimetric sensor in the quality evaluation of matcha Step 1 Sample Selection and Grading Matcha products purchased from Jiangsu Xinpin Tea Co. Ltd were selected as samples for the quality evaluation. Five grades (i.e., grades 1-5) were set.

Grade description: Matcha was graded according to standard DB32/T 751-2012, and matcha samples of different grades varied in appearance, inner quality and fresh leaf raw material.

Grade 1: the color was green and fresh; the particles were fine and even; the taste was fresh and seaweed aroma; the soup texture was even; and current-year-grown one bud with 2 or 3 leaves and the clip leaves with the same tenderness in the middle and late April and under the shade rate of 85% or above were used.

Grade 2: the color was green and fresh, the particles were fine and even; the taste was fresh and had pure fragrance; the soup texture was even; and current-year-grown one bud with 3 or 4 leaves, and clip leaves and tender single leaves with the same tenderness under the shade rate of 75% or above were used.

Grade 3: the color was tender and green; the particles were fine and even; the taste was refreshing, mellow and fragrant; the soup texture was even; and one bud with 2 or 3 fresh leaves were used.

Grade 4: the color was tender and green; the particles were fine and even; the taste was fresh, mellow and fragrant; the soup texture was even; and one bud of 2 or 3 leaves and clip leaves and tender single leaf with the same tenderness.

Grade 5: the color was tender and green; the particles were fine and even; the taste was fresh, mellow and fragrant; the soup texture was even; and one bud of 3 or 4 leaves and clip leaves and tender single leaf with the same tenderness.

Step 2 Image of the Nanoscaled Dye@ZIF-8-Based Colorimetric Sensor was Captured by a Camera.

The first image of the nanoscaled dye@ZIF-8-based colorimetric sensor before the reaction was captured by a camera.

Each of matcha reference samples was weighed with 5 g and placed in a reaction vessel together with the nanoscaled dye@ZIF-8-based colorimetric sensor. The nanoscaled dye@ZIF-8-based colorimetric sensor was fixed at the top of the reaction vessel to allow the nanoscaled dye@ZIF-8-based colorimetric sensor to react with volatile odorants released from the matcha reference samples at 40° C. for 12 min. The reaction vessel was kept sealed during the reaction.

The camera captured the second image of the reacted nanoscaled dye@ZIF-8-based colorimetric sensor and saved the second image in a computer.

Step 3 Construction of BPNN Model for Food Quality Evaluation

Each color-sensitive unit of the nanoscaled dye@ZIF-8-based colorimetric sensor was located by the computer from the first image and second image. The first and second images of the nanoscaled dye@ZIF-8-based colorimetric sensor before and after the reaction were decomposed into red (R)-channel, green (G)-channel, and blue (B)-channel grayscale sub-images. Differences between the gray mean values of each channel from each of color-sensitive units in the second image and gray mean values of each channel from each of color-sensitive units in the first image were obtained. The differences were expressed as: $\Delta R = R_a - R_b$, $\Delta G = G_a - G_b$, and $\Delta B = B_a - B_b$, where a subscript a represented the value from the second image, and a subscript b represented the value from the first image.

Euclidean distance was calculated, expressed as:

$$ED = \sqrt{\Delta R^2 + \Delta G^2 + \Delta B^2}.$$

$\Delta R$, $\Delta G$, $\Delta B$, and ED were feature variables of each of the color-sensitive units. 6 color-sensitive units had 24 feature variables. 5 matcha grades were set. Each grade contained 15 reference samples, and there were 75 reference samples in total. The 24 feature variables of each of the 75 reference samples were combined to obtain the feature matrix S (S was a 75×24 matrix). The BPNN model for matcha quality evaluation was constructed with the feature matrix S as input and the quality grade matrix T corresponding to the reference samples as output.

Figure 5A:
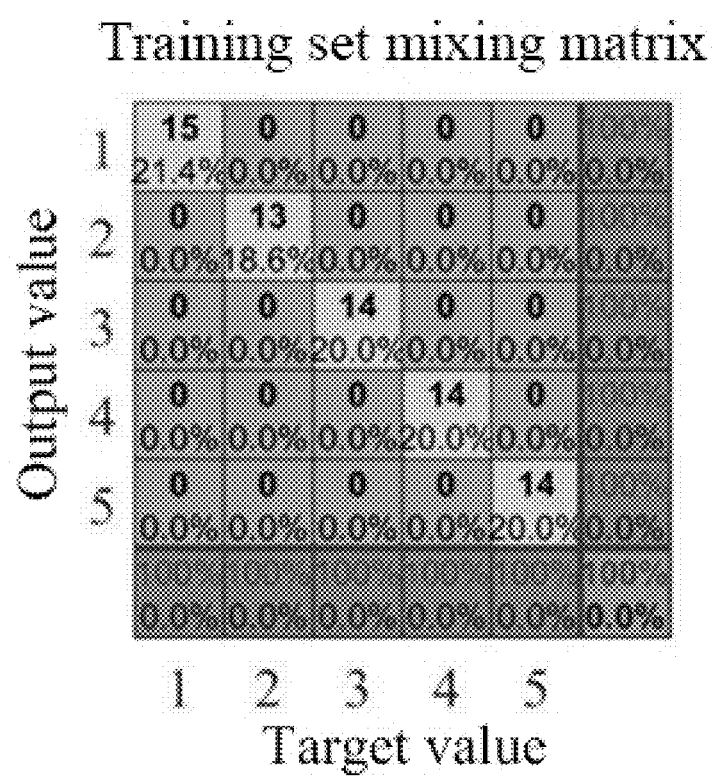
FIG. 5a shows training results of a BPNN model established in Embodiment 1 of the present disclosure for evaluation of matcha quality.

FIG. 5a showed training results of the BPNN model for evaluation of the matcha quality based on the sample information collected by the nanoscaled dye@ZIF-8-based colorimetric sensor, and the training accuracy of the evaluation model was 100%.

Step 4 Rapid Evaluation of Matcha Quality 15 to-be-tested matcha samples of unknown grade were taken. 24 feature variables of the 15 to-be-tested matcha samples were obtained in accordance with the method described in Steps 2 and 3 to construct a feature variable matrix R(R was a 15×24 matrix). The feature variable matrix R was input into the BPNN model constructed in Step 3 to generate the output matrix $Q$ corresponding to the quality grade information of the 15 to-be-tested matcha samples, thereby realizing rapid evaluation of matcha quality.

Figure 5B:
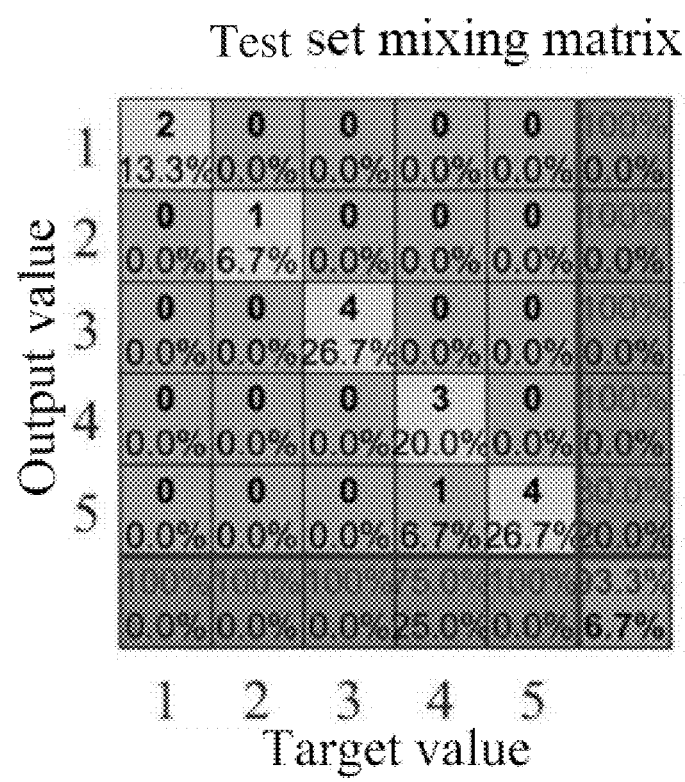
FIG. 5b shows evaluation results of matcha samples using the BPNN model in Embodiment 1 of the present disclosure.

FIG. 5b showed the evaluation results of the 15 to-be-tested matcha samples using the BPNN model. Compared to the results obtained from sensory evaluation, 14 of the 15 matcha samples were correctly predicted, indicating an accuracy rate of 93.3%. It confirmed that the nanoscaled dye@ZIF-8-based colorimetric sensor provided herein could realize the rapid evaluation of the matcha quality.

Embodiment 3

Quality evaluation method of snakehead fish during a storage period using the nanoscaled dye@ZIF-8-based colorimetric sensor Step 1 Sample Selection Snakehead fish samples were set with 4 grades according to the storage duration.

Grade description:
Grade 1: storage duration of 0 d at −18° C.;
Grade 2: storage duration of 3 d at −18° C.;
Grade 3: storage duration of 6 d at −18° C.;
Grade 4: storage duration of 9 d at −18° C.

Step 2 Image of the Nanoscaled Dye@ZIF-8-Based Colorimetric Sensor was Obtained by a Camera The first image of the nanoscaled dye@ZIF-8-based colorimetric sensor before the reaction was captured by a camera.

Each of snakehead fish reference samples was weighed with 10 g and placed in a reaction vessel together with the nanoscaled dye@ZIF-8-based colorimetric sensor. The nanoscaled dye@ZIF-8-based colorimetric sensor was fixed on the top of the reaction vessel to allow the nanoscaled dye@ZIF-8-based colorimetric sensor to react with volatile odorants released from the snakehead fish reference samples at room temperature for 10 min. The reaction vessel was kept sealed during reaction.

The camera captured the second image of the reacted nanoscaled dye@ZIF-8-based colorimetric sensor and saved the second image in a computer.

Step 3 Construction of BPNN Model for Food Quality Evaluation

Each of color-sensitive units of the nanoscaled dye@ZIF-8-based colorimetric sensor was located by the computer from the first image and second image. The first and second images of the nanoscaled dye@ZIF-8-based colorimetric sensor before and after the reaction were decomposed into R-channel, G-channel, and B-channel grayscale sub-images. Differences between the gray mean values of each channel from each of color-sensitive units in the second image and gray mean values of each channel from each of color-sensitive units in the first image were obtained. The differences were expressed as: $\Delta R = R_a - R_b$, $\Delta G = G_a - G_b$, and $\Delta B = B_a - B_b$, where a subscript a represents a grayscale value from the second image, and a subscript b represents a grayscale value from the first image.

Euclidean distance was calculated, expressed as:

$$ED = \sqrt{\Delta R^2 + \Delta G^2 + \Delta B^2}.$$

$\Delta R$, $\Delta G$, $\Delta B$, and ED were feature variables of each of the color-sensitive units. 6 color-sensitive units had 24 feature variables. Each quality grade contained 15 samples and there were 60 snakehead fish reference samples in total. The 24 feature variables of each of the 60 snakehead fish reference samples were combined to obtain the feature matrix S(S was a 60×24 matrix). The BPNN model for the snakehead fish quality evaluation was constructed with the feature matrix S as the input, and the quality grade matrix T corresponding to the reference samples as output.

Figure 6A:
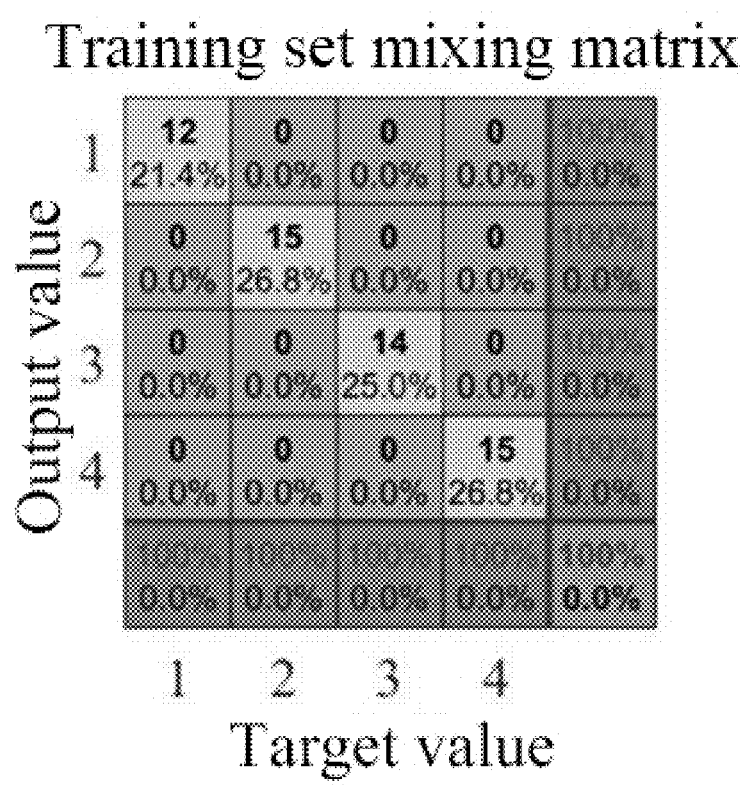
FIG. 6a shows training results of a BPNN model established in Embodiment 2 of the present disclosure for evaluation of snakehead fish quality.

FIG. 6a showed training results of the BPNN model for evaluation of the snakehead fish quality based on the sample information collected by the nanoscaled dye@ZIF-8-based colorimetric sensor, and the training accuracy of the evaluation model was 100%.

Step 4 Rapid Evaluation of Matcha Quality 10 to-be-tested snakehead fish samples of unknown grade were taken. 24 feature variables of the 10 to-be-tested snakehead fish samples to be tested were obtained in accordance with the method described in Steps 2 and 3 to construct a feature variable matrix R(R was a 10×24 matrix). The feature variable matrix R was input into the BPNN model constructed in Step 3 to generate the output matrix $Q$ corresponding to the quality grade information of the 10 to-be-tested snakehead fish samples, thereby realizing the rapid evaluation of food quality.

Figure 6B:
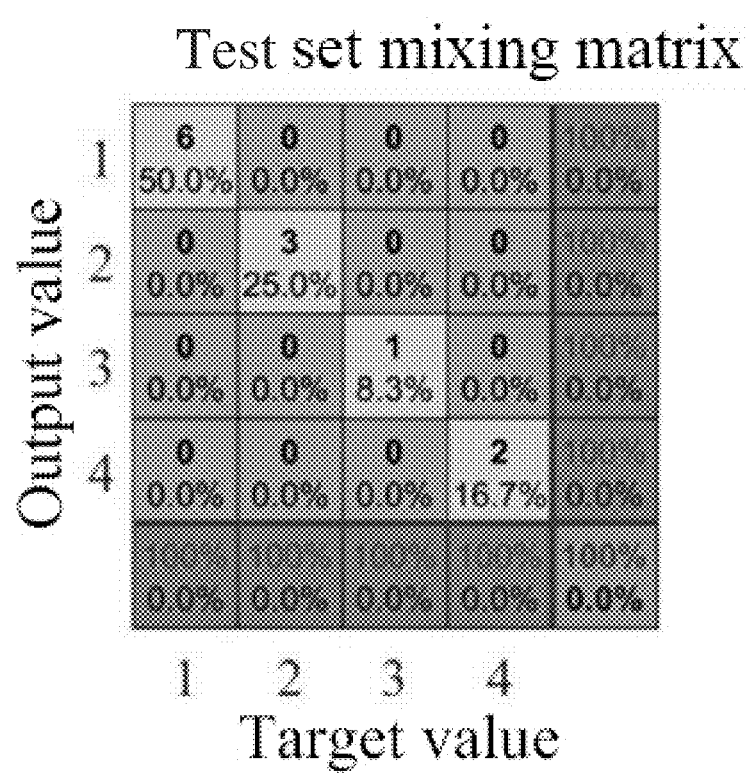
FIG. 6b shows evaluation results of snakehead fish samples using the BPNN model established in Embodiment 2 of the present disclosure.

FIG. 6b showed the evaluation results of the 10 to-be-tested snakehead fish samples using the BPNN model. Compared to the results obtained from Kjeldahl nitrogen determination method, all the 10 samples were correctly predicted, indicating an accuracy rate of 100%. It confirmed that the nanoscaled dye@ZIF-8-based colorimetric sensor in this disclosure could realize the rapid evaluation of the snakehead fish quality.

Described above are merely preferred embodiments of the disclosure, which are not intended to limit the disclosure. It should be understood that any modifications and replacements made by those skilled in the art without departing from the spirit of the disclosure should fall within the scope of the disclosure defined by the appended claims.

What is claimed is:

1. A method for preparing a nanoscaled dye@ZIF-8-based colorimetric sensor, comprising:
   (a) dissolving $Zn(CH_3COO)_2 \cdot 2H_2O$ in deionized water to obtain a $Zn(CH_3COO)_2$ solution, wherein a ratio of a weight of the $Zn(CH_3COO)_2 \cdot 2H_2O$ to a volume of the deionized water is 2.70 g:45 mL; and dissolving 2-methylimidazole in deionized water to obtain a 2-methylimidazole solution, wherein a ratio of a weight of the 2-methylimidazole to a volume of the deionized water is 22.23 g:100 mL;
   (b) mixing the $Zn(CH_3COO)_2$ solution and the 2-methylimidazole solution following by stirring and standing to obtain a precipitate, wherein a volume ratio of the $Zn(CH_3COO)_2$ solution to the 2-methylimidazole solution is 45:57.6; and subjecting the precipitate to centrifugal washing respectively with water and ethanol and drying to obtain a zeolitic imidazolate framework-8 (ZIF-8) nanomaterial;
   (c) dispersing the ZIF-8 nanomaterial with ethanol to obtain a ZIF-8 dispersion with a concentration of 2 mg/ml;
   (d) preparing a colorimetric solution with a concentration of 2 mg/mL, wherein the colorimetric solution is a pH indicator ethanol solution or a metalloporphyrin dichloromethane solution; a ratio of a weight of a pH indicator to a volume of ethanol in the pH indicator ethanol solution is 20 mg:10 mL; a ratio of a weight of a metalloporphyrin compound to a volume of dichloromethane in the metalloporphyrin dichloromethane solution is 20 mg:10 mL; the pH indicator is selected from the group consisting of cresol red, brilliant yellow, and neutral red; and the metalloporphyrin compound is selected from the group consisting of 2, 3, 7, 8, 12, 13, 17, 18-octaethyl-21H, 23H-porphine nickel (II), 5, 10, 15, 20-tetraphenyl-21H,23H-porphine zinc, and 5, 10, 15, 20-tetrakis(pentafluorophenyl)-21H, 23H-porphyrin iron (III) chloride;
   (e) mixing the colorimetric solution with the ZIF-8 dispersion in a volume ratio of 1:1 to obtain a mixed solution; and
   (f) adding polyethylene glycol-300 to the mixed solution followed by ultrasonic treatment to obtain a nanoscaled dye@ZIF-8 colorimetric material, wherein the polyethylene glycol-300 is 20% by volume of the mixed solution; and fixing the nanoscaled dye@ZIF-8 colorimetric material on a substrate to obtain the nanoscaled dye@ZIF-8-based colorimetric sensor.

2. The method of claim 1, wherein in step (b), the stirring is performed for 10-20 min; the standing is performed for 2-6 h; and the centrifugal washing is performed 3-5 times.

3. The method of claim 1, wherein in step (f), the ultrasonic treatment is performed at 40° C. for 30-50 min; a volume of the nanoscaled dye@ZIF-8 colorimetric material applied to the substrate is 1.5-2 μL; and the substrate is a silica gel plate, a Polyvinylidene Fluoride (PVDF) membrane, or a mixed cellulose ester.

4. A use of a nanoscaled dye@ZIF-8-based colorimetric sensor prepared by the method of claim 1 for food quality evaluation, comprising:
   (A) selecting a plurality of reference samples respectively at a plurality of quality grades, wherein the plurality of quality grades respectively correspond to different volatile odorants; the nanoscaled dye@ZIF-8-based colorimetric sensor is configured to present different colors respectively in the presence of the different volatile odorants;
   each of the plurality of reference samples is an agricultural product or an aquatic product; and an indicator for characterizing the plurality of quality grades is freshness or sensory quality;
   (B) capturing, by a camera, the nanoscaled dye@ZIF-8-based colorimetric sensor to obtain a first image;
   respectively placing the plurality of reference samples in a reaction vessel with the nanoscaled dye@ZIF-8-based colorimetric sensor to allow the nanoscaled dye@ZIF-8-based colorimetric sensor to react with volatile odorants respectively released from the plurality of reference samples, wherein the reaction vessel is kept sealed during a reaction;
   capturing, by the camera, a reacted nanoscaled dye@ZIF-8-based colorimetric sensor to obtain a second image, and saving the second image in a computer;
   locating, by the computer, each of color-sensitive units of the nanoscaled dye@ZIF-8-based colorimetric sensor respectively from the first image and the second image; extracting a color feature of each of the color-sensitive units; and obtaining a difference in grayscale value for each channel before and after the reaction from each of the color-sensitive units as feature variables of each of the color-sensitive units; and
   combining feature variables of the plurality of reference samples to obtain a feature matrix; and constructing a back propagation neural network (BPNN) model with the feature matrix as an input and the plurality of quality grades as an output as a food quality evaluation model; and
   (C) reacting a to-be-tested sample with the nanoscaled dye@ZIF-8-based colorimetric sensor according to the step (B) to obtain a feature variable of the to-be-tested sample; and inputting the feature variable of the to-be-tested sample into the BPNN model to obtain quality grade information of the to-be-tested sample, and evaluating quality of the to-be-tested sample based on the quality grade information.

5. The use of claim 4, wherein in the step (B), when the plurality of reference samples are agricultural products, an amount of each of the plurality of reference samples added to the reaction vessel is 2-5 g; when the plurality of reference samples are aquatic products, an amount of each of the plurality of reference samples added to the reaction vessel is 10-15 g; the nanoscaled dye@ZIF-8-based colorimetric sensor is reacted with the volatile odorants for 10-20 min; and the nanoscaled dye@ZIF-8-based colorimetric sensor is provided at a top of the reaction vessel.

6. The use of claim 4, wherein in the step (B), the feature variables of each of the color-sensitive units is extracted through steps of:

locating, by the computer, each of the color-sensitive units;

decomposing each of the first image and the second image into three grayscale images respectively representing a red (R)-channel grayscale sub-image, a green (G)-channel grayscale sub-image, and a blue (B)-channel grayscale sub-image;

obtaining the difference in grayscale value for each channel before and after the reaction from each of the color-sensitive units, expressed as: $\Delta R=R_a-R_b$, $\Delta G=G_a-G_b$, and $\Delta B=B_a-B_b$, wherein a subscript a represents a grayscale value from the second image, and a subscript b represents a grayscale value from the first image; and calculating a Euclidean distance, expressed as:

$$ED = \sqrt{\Delta R^2 + \Delta G^2 + \Delta B^2};$$

wherein $\Delta R$, $\Delta G$, $\Delta B$, and ED are the feature variables of each of the color-sensitive units; when the number of the color-sensitive units is X, there are a total of Y feature variables, wherein Y=4X; and the number of the plurality of reference samples for constructing the food quality evaluation model is N; the number of the plurality of quality grades is n; and the number of reference samples in each of the plurality of quality grades is m, N=n×m; n is a positive integer not less than 2; and both m and N are positive integers.

7. The use of claim 4, wherein in the step (B), the food quality evaluation model is built through steps of:

constructing the feature matrix S, wherein S=N×Y, N represents the number of the plurality of reference samples, and Y represents the number of feature variables in X color-sensitive units; and constructing the BPNN model with the feature matrix S as the input and a quality grade matrix T corresponding to the plurality of reference samples as the output;

wherein the feature matrix S is expressed as:

$$S = \begin{bmatrix} S_{11} & S_{12} & \cdots & S_{1Y} \\ S_{21} & S_{22} & \cdots & S_{2Y} \\ \vdots & \vdots & \vdots & \vdots \\ S_{N1} & S_{N2} & \cdots & S_{NY} \end{bmatrix};$$

and the quality grade matrix T is expressed as:

$$T = \begin{bmatrix} T_{11} \\ T_{21} \\ \vdots \\ T_{N1} \end{bmatrix}.$$

8. The use of claim 4, wherein the step (C) is performed through steps of:

obtaining the feature variable of the to-be-tested sample according to the step (B), wherein the number of the to-be-tested sample is M, and the number of the feature variable of each of M to-be-tested samples is Y; and constructing a feature variable matrix R, wherein R=M×Y; and inputting the feature variable matrix R into the BPNN model constructed in the step (B) to generate an output matrix Q corresponding to quality grade information of the M to-be-tested samples for food quality evaluation;

wherein the feature variable matrix R is expressed as:

$$R = \begin{bmatrix} R_{11} & R_{12} & \cdots & R_{1Y} \\ R_{21} & R_{22} & \cdots & R_{2Y} \\ \vdots & \vdots & \vdots & \vdots \\ R_{M1} & R_{M2} & \cdots & R_{MY} \end{bmatrix};$$

and the output matrix Q is expressed as:

$$Q = \begin{bmatrix} Q_{11} \\ Q_{21} \\ \vdots \\ Q_{M1} \end{bmatrix}$$

* * * * *